US005734040A

United States Patent [19]
Weeks et al.

[11] Patent Number: 5,734,040
[45] Date of Patent: Mar. 31, 1998

[54] POSITIVELY CHARGED OLIGONUCLEOTIDES AS REGULATORS OF GENE EXPRESSION

[75] Inventors: Daniel L. Weeks; John Dagle, both of Iowa City, Iowa

[73] Assignee: University of Iowa Research Foundation, Iowa City, Iowa

[21] Appl. No.: 619,301

[22] Filed: Mar. 21, 1996

[51] Int. Cl.⁶ .................... C07H 21/04; C12N 15/85
[52] U.S. Cl. .................. 536/24.5; 435/325; 536/23.1
[58] Field of Search .................. 536/24.5; 435/240.2; 514/44

[56] References Cited

U.S. PATENT DOCUMENTS

| | | | |
|---|---|---|---|
| 5,175,266 | 12/1992 | Varma et al. | 536/22 |
| 5,176,996 | 1/1993 | Hogan et al. | 435/6 |
| 5,194,654 | 3/1993 | Hostetler et al. | 558/152 |
| 5,476,925 | 12/1995 | Letsinger et al. | 536/23.1 |
| 5,489,677 | 2/1996 | Sanghvi et al. | 536/22.1 |

FOREIGN PATENT DOCUMENTS

| | | | |
|---|---|---|---|
| WO 90/14074 | 11/1990 | WIPO | A61K 9/127 |
| WO 92/10590 | 6/1992 | WIPO | C12Q 1/68 |
| WO 93/07295 | 4/1993 | WIPO | C12Q 1/68 |
| WO 93/10820 | 6/1993 | WIPO | A61K 48/00 |
| WO 93/24507 | 12/1993 | WIPO | C07H 17/00 |
| WO 94/11524 | 5/1994 | WIPO | C12P 21/00 |
| WO 94/24144 | 10/1994 | WIPO | C07H 21/00 |
| WO 95/17373 | 6/1995 | WIPO | C07C 211/63 |
| WO 95/20404 | 8/1995 | WIPO | A61K 48/00 |

OTHER PUBLICATIONS

Horn T, et al. "Oligonucleotides with alternating anionic and cationic phosphoramidate linkages: synthesis and hybridization of sterio–uniform isomers," *Tetrahedron Letters* 37: 743–746, Feb. 5, 1996.

Beal PA, et al. "Second structural motif for recognition of DNA by oligonucleotide–directed triple–helix formation," *Science* 251: 1360–1363, Mar. 15, 1991.

Williamson JR, et al. "Monovalent cation–induced structure of telomeric DNA: The G–quartet model." *Cell* 59:871–880, Dec. 1, 1989.

Olivas WM, et al. "Overcoming potassium–mediated triplex inhibition," *Nucleic Acids Res.* 23: 1936–1941, 1995.

Stull RA, et al. "Antigene, ribozyme and aptamer nucleic acid drugs: Progress and prospects." *Pharmaceutical Res.* 465–483, 1995.

F.K. Askari et al., "Molecular Medicine Antisense–Oligonucleotide Therapy", *New Engl. J. Med.*, 334 316–318 (1996).

P.A. Beal et al., "Second Structural Motif for Recognition of DNA by Oligonucleotide–Directed Triple–Helix Formation", *Science*, 251 1360–1363 (1991).

B.L. Brizzard et al., "Immunoaffinity Purification of FLAG Epitope–Tagged Bacterial Alkaline Phosphatase Using a Novel Monoclonal Antibody and Peptide Elution", *BioTechniques*, 16 730–735 (1994).

D.A. Brown et al., "Effect of Phosphorothioate Modification of Oligodeoxynucleotides on Specific Protein Binding", *J. of Biological Chemistry*, 269 26801–26805 (1994).

S.A. Cassidy et al., "Effect of a Triplex–Binding Ligand on Parallel and Antiparallel DNA Triple Helices Using Short Unmodified and Acridine–Linked Oligonucleotides", *Biochem.*, 33 15338–15347 (1994).

S. Chaturvedi et al., "Stabilization of triple–stranded oligonucleotide complexes: use of probes containing alternating phosphodiester and stereo–uniform cationic phosphoramidate linkages", *Nucleic Acids Research*, 24 2318–2323 (1996).

M. Cooney et al., "Site–Specific Oligonucleotide Binding Represses Transcription of the Human c–myc Gene in Vitro", *Science*, 241 456–459 (1988).

J.M. Dagle, "Positively Charged Oligonucleotides Overcome Potassium–Mediated Inhibition of Triplex DNA Formation", Abstract Serial No. 12833, Submitted to APS/SPR Program Office prior to Mar. 21, 1996.

J.M. Dagle et al., "Targeted degradation of mRNA in Xenopus oocytes and embryos directed by modified oligonucleotides: studies of An2 and cyclin in embryogenesis", *Nucleic Acids Research*, 18 4751–4757 (1990).

J.M. Dagle et al., "Pathways of Degradation and Mechanism of Action of Antisense Oligonucleotides in *Xenopus iaevis* Embryos", *AntiSense Research and Development*, 1 11–20 (1991).

R.H. Durland et al., "Binding of Triple Helix Forming Oligonucleotides to Sites in Gene Promoters", *Biochem.*, 30 9246–9255 (1955).

R.H. Durland et al., "Binding of T and T analogs to CG base pairs in anitparallel triplexes", *Nucleic Acids Research*, 22 3233–3240 (1994).

R. Fathi et al., "Oligonucleotides with novel, cationic backbone substituents: aminoethylphosphonates", *Nucleic Acids Research*, 22 5416–5424 (1994).

B.C. Froehler et al., "Synthesis of DNA via deoxynucleoside H–phosphonate intermediates", *Nucleic Acids Research*, 14 5399–5407 (1986).

J.E. Fulton et al., "Functional analysis of avian class I (BFIV) glycoproteins by epitope tagging and mutagenesis in vitro" , *Eur. J. Immunol.*, 25 2069–2076 (1995).

J.E. Gee et al., "Structure and Applications of Intermolecular DNA Triplexes", *Med. Sciences*, 304 366–372 (1992).

(List continued on next page.)

*Primary Examiner*—George C. Elliott
*Assistant Examiner*—Amy J. Nelson
*Attorney, Agent, or Firm*—Mueting, Baasch, Gebhardt & Schwappach, P.A.

[57] ABSTRACT

This invention relates to oligonucleotides with ethylenediamine phosphoramidate internucleoside linkages useful for binding to eukaryotic duplex DNA to inhibit or alter gene expression.

23 Claims, 1 Drawing Sheet

OTHER PUBLICATIONS

C. Giovannangeli et al., "Oligonucleotide clamps arrest DNA synthesis on a single-stranded DNA target", *Proc. Natl. Acad. Sci. USA*, 90 10013–10017 (1993).

M.A. Guvakova et al., "Phosphorothioate Oligodeoxynucleotides Bind to Basic Fibroblast Growth Factor, Inhibit Its Binding to Cell Surface Receptors, and Remove It from Low Affinity Binding Sites on Extracellular Matrix", *J. of Bio. Chem.*, 270 2620–2627 (1995).

T. Horn et al., "Oligonucleotides with Alternating Anionic and Cationic Phosphoramidate Linkages: Synthesis and Hybridization of Stereo–uniform Isomers", *Tetrahedron Letters*, 37 743–746 (1996).

S.D. Jayasena et al., "Intramolecular Triple–Helix Formation at $(Pu_nPy_n) \bullet (Pu_nPy_n)$ Tracts: Recognition of Alternate Strands via Pu•PuPy and Py•PuPy Base Triplets", *Biochem.*, 31 320–327 (1992).

S.D. Jayasena et al., "Oligonucleotide–directed triple helix formation at adjacent oligopurine and oligopyrimidine DNA tracts by alternate strand recognition", *Nucleic Acids Research*, 20 5279–5288 (1992).

D.H. Jones et al., "A Rapid Method for Recombination and Site–Specific Mutagenesis by Placing Homologous Ends on DNA Using Polymerase Chain Reaction", *BioTechniques*, 10 62–66 (1991).

H.G. Kim et al., "Inhibition of in Vitro Transcription by a Triplex–Forming Oligonucleotide Targeted to Human c–myc P2 Promoter", *Biochem.* 34 8165–8171 (1995).

J. Klysik, "Cruciform Extrusion Facilitates Intramolecular Triplex Formation between Distal Oligopurine•Oligopyrimidine Tracts: Long Range Effects", *J. of Bio. Chem.*, 267 17430–17437 (1992).

S.H. Krawczyk et al., "Oligonucleotide–mediated triple helix formation using an $N^3$–protonated deoxycytidine analog exhibiting pH–independent binding within the physiological range", *Proc. Natl. Acad. Sci. USA*, 89 3761–3764 (1992).

T. LeDoan et al., "Sequence–specific recognition, photo-crosslinking and cleavage of the DNA double helix by an oligo[α]–thymidylate convalently linked to an azidoproflavine derivative", *Nucleic Acids Research*, 15 7749–7760 (1987).

R.L. Letsinger et al., "Cationic Oligonucleotides", *J. of Amer. Chem. Soc.*, 110 4470–4471 (1988).

V.I. Lyamichev et al., "A stable complex between homopyrimidine oligomers and the homologous regions of duplex DNAs", *Nucleic Acids Research*, 16 2165–2178 (1988).

V.M. Macaulay et al., "Inhibition of aromatase expression by a psoralen–linked triplex-forming oligonucleotide targeted to a coding sequence", *FEBS Letters*, 372 222–228 (1995).

L.J. Maher III et al., "Inhibition of DNA/Protein Interactions by Oligonucleotide–Directed DNA Triple Helix Formation: Progress and Prospects", *Prospects for Antisense Nucleic Acid Therapy of Cancer and AIDS*, 227–242 (1991).

H.E. Moser et al., "Sequence–Specific Cleavage of Double Helical DNA by Triple Helix Formation", *Science*, 238 645–650 (1987).

M. Musso et al., "Polyamine effects on purine–purine–pyrimidine triple helix formation by phosphodiester and phosphorothioate oligodeoxyribonucleotides", *Nucleic Acids Research*, 23 2320–2327 (1995).

W.M. Olivas et al., "Overcoming potassium–mediated triplex inhibition", *Nucleic Acids Research*, 23 1936–1941 (1995).

W.M. Olivas et al., "Competitive Triplex–Quadruplex Equilibria Involving Guanine–Rich Oligonucleotides", *Biochem.*, 34 278–284 (1995).

Z. Oláh et al., "A Cloning and ε–Epitope–Tagging Insert for the Expression of Polymerase Chain Reaction–Generated cDNA Fragments in *Escherichia coli* and Mammalian Cells", *Anal. Biochem.*, 221 94–102 (1994).

F.M. Orson et al., "Linkage structures strongly influence the binding cooperativity of DNA intercalators conjugated to triplex forming oligonucleotides", *Nucleic Acids Research*, 22 479–484 (1994).

N. Ovsenek et al., "A maternal factor, OZ–1, activates embryonic transcription of the *Xenopus iaevis* GS17 gene", *Development*, 115 649–655 (1992).

K.S. Prickett et al., "A Calcium–Dependent Antibody for Identification and Purification of Recombinant Proteins", *BioTechniques*, 7 580–589 (1989).

P. Rajagopal et al., "Triple–strand formation in the homopurine–homophyrimidine DNA oligonucleotides $d(G-A)_4$ and $d(T-C)_4$", *Nature*, 339 637–640 (1989).

M.R. Rebagliati et al., "Antisense RNA Injections in Fertilized Frog Eggs Reveal an RNA Duplex Unwinding Activity", *Cell*, 48 599–605 (1987).

T. Sudhakar Rao et al., "Incorporation of 2'–Deoxy–6–thioguanosine into G–Rich Oligodeoxyribonucleotides Inhibits G–Tetrad Formation and Facilitates Triplex Formation", *Biochem.*, 34 765–772 (1995).

T.J. Stonehouse et al., "DNase I footprinting of triple helix formation at polyprine tracts by acridine–linked oligopyrimidines: stringency, structural changes and interaction with minor groove binding ligands", *BBA*, 1218 322–330 (1994).

C.H. Tung et al., "Polyamine–linked oligonucleotides for DNA triple helix formation", *Nucleic Acids Research*, 21 5489–5494 (1993).

D.L. Weeks et al., "Cyclin B mRNA depletion only transiently inhibits the Xenopus embyonic cell cycle", *Development*, 111 1173–1178 (1991).

J.R. Williamson et al., "Monovalent Cation–Induced Structure of Telomeric DNA: The G–Quartet Model", *Cell*, 59 871–880 (1989).

W.D. Wilson et al., "DNA Triple–Helix Specific Intercalators As Antigene Enhancers: Unfused Aromatic Cations", *Biochem.*, 32 10614–10621 (1993).

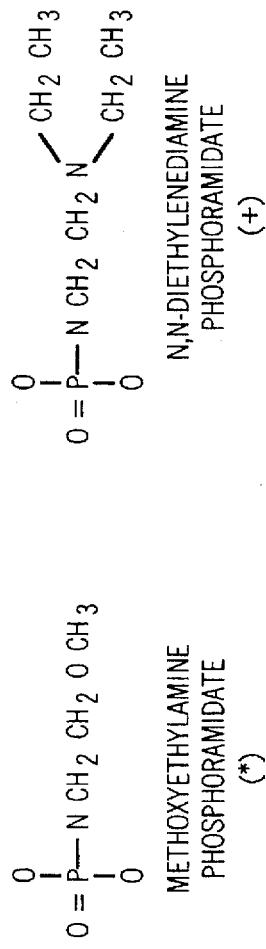

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

AGTTTTGTGT CCCCCTCTCA GGTGTCACAG     3 0

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:2:

AAAATATAGG GGGAGAG    17

(2) INFORMATION FOR SEQ ID NO:3:

(i) SEQUENCE CHARACTERISTICS:
 (A) LENGTH: 30 base pairs
 (B) TYPE: nucleic acid
 (C) STRANDEDNESS: double
 (D) TOPOLOGY: linear (i i) MOLECULE TYPE: DNA (genomic)

(x i) SEQUENCE DESCRIPTION: SEQ ID NO:3:

GCCCCCTGGC CCCTCCCCTT TGTTCCATTT    30

(2) INFORMATION FOR SEQ ID NO:4:

(i) SEQUENCE CHARACTERISTICS:
 (A) LENGTH: 23 base pairs
 (B) TYPE: nucleic acid
 (C) STRANDEDNESS: single
 (D) TOPOLOGY: linear (i i) MOLECULE TYPE: DNA (genomic)

(x i) SEQUENCE DESCRIPTION: SEQ ID NO:4:

AGGGAGGGAG GTAAGAAAAA GGG    23

(2) INFORMATION FOR SEQ ID NO:5:

(i) SEQUENCE CHARACTERISTICS:
 (A) LENGTH: 23 base pairs
 (B) TYPE: nucleic acid
 (C) STRANDEDNESS: single
 (D) TOPOLOGY: linear (i i) MOLECULE TYPE: DNA (genomic)

(x i) SEQUENCE DESCRIPTION: SEQ ID NO:5:

GGGAAAAAGA ATGGAGGGAG GGA    23

POSITIVELY CHARGED OLIGONUCLEOTIDES AS REGULATORS OF GENE EXPRESSION

The present invention was made with government support from the National Institutes of Health Grant No. HL 42266. The government has certain rights to this invention.

FIELD OF THE INVENTION

This invention relates to oligonucleotides used to control gene expression or other cellular events. In particular this invention relates to oligonucleotides with cationic phosphoramidate internucleoside linkages.

BACKGROUND OF THE INVENTION

Synthetic oligonucleotides have been shown to regulate gene expression in cells. Thus, these molecules bind to target regions of nucleic acids and inhibit gene expression. They are useful to control infectious disease and have been used and tested in a variety of diseases or conditions associated with altered or aberrant gene expression such as cancers, hereditary disorders, and the like.

There are two major oligonucleotide (ODN) based strategies designed to inhibit gene expression. One method uses antisense ODNs complementary to a specific mRNA to form DNA:RNA hybrids. These hybrids are stabilized by Watson-Crick base pairing and are substrates for cellular ribonuclease H (RNase H), an enzyme that degrades the RNA portion of the duplex rendering the mRNA untranslatable (Walder, et al. *Proc. Natl. Acad. Sci. USA* 85:5011–5015, 1988). Because RNase H does not degrade the ODN, the ODN is able to hybridize to another copy of the target mRNA.

A second ODN-based strategy for altering gene expression targets DNA by the formation of a triple helical structure. The use of ODNs to form triple helix structures was initially reported by Moser, et al. (*Science* 238:645–650, 1987 and see LeDoan, et al. *Nucl. Acids Res.* 15:7749–7760, 1987). Under suitable conditions, an ODN will bind in the major groove of a DNA duplex. The presence of a third strand may either sterically block transcription, prevent the sequence specific interactions of regulatory proteins with DNA and/or alter the conformation of the bound duplex.

There are two known triplex binding motifs, both involving interactions between the bases of a relatively short ODN (generally between 11–50 base pairs) and the purine bases of a polypurine:polypyrimidine stretch of duplex DNA. In the pyrimidine motif, thymidine residues in the third strand interact with adenosine residues of an A:T duplex while a protonated cytidine in the third strand is hydrogen-bonded to the guanosine of a G:C duplex (Moser, et al. supra). The protonation of C residues at nitrogen position number three generally requires a pH less than six, and thus limits the use of this strategy in vivo (Rajagopal, P. et al. *Nature* 339:637–640, 1989 and Lyamichev, et al. *Nucl. Acids Res.* 16: 2165–2178, 1988) unless deoxycytidine analogues are used (see Krawczyk, et al. *Proc. Natl. Acad. Sci. (USA)*, 89:3761–3764, 1992).

The second triplex motif involves a purine rich triplex forming oligonucleotide (TFO). Thymidine or adenosine residues of the third strand bind to the adenosine of an A:T duplex and guanosine in the third strand interacts with the guanosine of a G:C duplex (Beal, et al. *Science* 251:1360–1363, 1991; Durland, et al. *Biochem.* 30:9246–9255, 1955 and Cooney, et al. *Science* 241:456–459, 1988). The orientation of the third strand has been shown to be antiparallel to the purine-rich strand of the duplex (Beal, et al. supra). Preferred methods employing this strategy use ODNs modified to produce a net neutral charge. The major drawback to using this approach in vivo is the tendency of G-rich ODNs to self-associate into quartets at physiologic potassium concentrations. However, recent studies indicate that the use of a GT rich ODN to affect transcription of a transfected CAT plasmid in vivo indicates that GT rich combinations may minimize quartet formation. Unmodified negatively charged oligonucleotides do not generally stably participate in triplex formation in cells. Triplex forming oligonucleotide strategies must account for the physiologic concentrations of $Mg^{+2}$ and the level of potassium tolerated for stable triplex formation.

To improve the stability and cellular uptake of oligonucleotides, oligonucleotides have been prepared having modifications to the phosphate backbone. For example, phosphorothiate and methylphosphonate derivatives of oligonucleotides have been synthesized and have sequence specificity and strength of hybridizations similar to that of unmodified oligonucleotides. Aminoethyl phosphonate derivatives of oligonucleotides have also been synthesized and demonstrate enhanced stability in aqueous solution as compared with aminomethylphosphonate linkages (Fathi, et al. *Nucl. Acids Res.* 22:5416–5424, 1994). The uncharged character of the methylphosphonate derivatives permits an enhanced uptake of the oligonucleotides by the cell and increased resistance to nucleases as compared with unmodified oligonucleotides. Methoxyethyl-phosphoramidate linkages that have been incorporated into the internucleoside backbone at 3' and 5' linkages to inhibit exonuclease degradation. The synthesis of ODNs with some modified and some unmodified linkages allowed both increased nuclease resistance while maintaining RNase H mediated target RNA degradation. (Dagle, et al. *Antisense Res. and Devel.* 1:11–20, 1991).

Intercalating agents have also been conjugated to oligonucleotides to increase the stability of the conjugate with the complementary strand (see for example, Wilson, et al. *Biochem.* 32:10614–10621, 1993 and Orson, et al. *Nucl. Acids Res.* 22:479–484, 1994). In addition, molecules are often attached to the oligonucleotides to modify the net charge. Examples of these agents include polylysine, cationic peptides, polyamines and polycationic polymers. Intercalators and polylysine have shown an increased resistance to nuclease degradation.

Nucleomonomers can also be modified to improve triplex formation and PCT International Publication No. WO 94/24144 discloses oligomers with 7-deaza-7-substituted purines.

The formation of a DNA triplex using a purine rich ODN is inhibited by monovalent cations, particularly potassium ions (Olivas, et al. *Biochem.* 34:278–284, 1995). Intracellular $K^+$ concentrations inhibit triplex formation using unmodified oligonucleotides. Potassium ions are the predominant intracellular cations. One problem with forming triplexes at physiologic $K^+$ levels is the self association of guanosine-rich ODNs into aggregates which are stabilized by guanine quartets (Olivas, et al. *Biochem.* 34:278–284, 1995; Olivas, et al. *Nucl. Acids Res.* 23:1936–1941, 1995). In addition to decreasing the rate of triplex association, $K^+$ increases the rate of triplex dissociation in vitro (Olivas, *Biochem.* supra). The inhibitory effect of $K^+$ can be partially diminished by chemical modification of ODNs. For example, incorporation of the modified base 6-thioguanine in place of native guanine into TFOs decreases the association of ODNs into quartets and increases triplex formation in the presence of monovalent cations (Olivas, *Nucl. Acids Res.*, supra and Rao, et al. *Biochem.* 34:765–772, 1995).

Another hurdle associated with the use of ODNs in vivo is that the oligonucleotides are rapidly degraded by intracellular nucleases (Rebagliata, eta. *Cell* 48:599–605, 1987; Dagle, et al. *Nucl. Acids. Res.* 18:4751–4757, 1990; Dagle, et al. *Antisense Res. and Dev.* 1:11–20, 1991). The chemical modification of ODNs provides resistance to nucleolytic degradation (Dagle, et al. supra), potentially increasing the overall activity of these compounds in vivo (Dagle, et al. supra and Weeks, et al. *Development* 111:1173–1178, 1991). The type and degree of chemical modification of ODNs, however, is limited when strategies require the action of cellular RNase H (Dagle, et al. *Antisense*, supra). Additionally, some modification of ODNs can result in nonspecific toxicity mediated through non-nucleic acid interactions, such as has recently been reported for phosphorothioate ODNs and the basic fibroblast growth factor receptor (Guvakova, et al. *J. Biol. Chem.* 270:2620–2627, 1995). In contrast, the formation of triplex structures does not require an enzymatic activity and thus allows greater flexibility with regard to ODN design. The enhanced nucleolytic stability of an ODN with many or all internucleoside linkages modified would be useful for in vivo applications if these compounds are able to form stable triplex structures. The present invention discloses a class of oligonucleotides with enhanced stability for triplex formation.

Candidate oligonucleotides should produce triplex formation at physiologic salt concentrations. The close association of two nucleic acid strands creates a highly negatively charged environment. Many oligonucleotides disclosed in the literature to date require the presence of magnesium ions above physiologic concentrations to produce stable triplex formation. The obligate presence of magnesium ions for triplex association most likely reduces interstrand charge repulsions. However, magnesium concentrations within the cell cannot be altered without altering cell physiology. Therefore, oligonucleotides dependent on minimum concentrations of magnesium ions may not function well in the cellular milieu. Neutral phosphate analogs as well as the oligonucleotides of this invention do not require this type of magnesium dependence but binding of neutral charged oligonucleotides to duplex DNA is inhibited by physiologic $K^+$ concentrations.

The present invention discloses a class of oligonucleotides that strongly enhance triplex formation even in the presence of $K^+$ ion concentrations exceeding physiologic levels.

SUMMARY OF THE INVENTION

The present invention relates to the selection, production and use of oligonucleotides with cationic phosphoramidate modified internucleoside linkages to form stable triplex DNA structures to inhibit gene expression.

In one embodiment of this invention an oligonucleotide is disclosed having cationic phosphoramidate internucleoside linkages. The cationic phosphoramidate is incorporated during oligonucleotide synthesis via oxidative amidation and in a preferred embodiment the cationic phosphoramidate has both a primary and a tertiary amine. Preferably the oligonucleotide is about 15–30 nucleotides in length. In one embodiment the oligonucleotide has ethyl-ethylenediamine internucleoside linkages and preferably these linkages are N,N-diethyl-ethylenediamine internucleoside linkages. In one embodiment about 30 to about 100% of the internucleoside linkages are N,N-diethyl-ethylenediamine and still more preferably there are about 60 to about 100% N,N-diethyl-ethylenediamine linkages. The oligonucleotide can be either purine or pyrimidine rich. Preferably where the oligonucleotide is purine rich, the purines are GA rich.

Where the oligonucleotide is purine rich, the oligonucleotide preferably binds to the double stranded DNA antiparallel to the purine rich strand.

The cationic phosphoramidate substituted oligonucleotides of this invention preferably bind to double stranded DNA under physiologic conditions including physiologic solutions such as are found within a cell and preferably the oligonucleotides are able to bind to double stranded DNA in a physiologic solution comprising a $K^+$ concentration of about 100–250 mM. The oligonucleotides of this invention can also include base modifications and a preferred base modification is 6-thioguanosine.

In another aspect of this invention, the invention relates to a method of altering transcription from a gene in a eukaryotic cell comprising the steps of preparing an oligonucleotide with at least one cationic phosphoramidate internucleoside linkage capable of binding to a purine motif in a regulatory region operably linked to a gene comprising duplex DNA wherein the regulatory region regulates gene expression, introducing the oligonucleotide into a eukaryotic cell contain the regulatory regions, wherein the oligonucleotide binds to the regulatory region of duplex DNA and detecting altered transcription from the gene. Preferably the cationic phosphoramidate internucleoside linkage was prepared using N, N-diethyl-ethylenediamine and the oligonucleotide is about 15 to about 30 nucleotides in length.

FIGURES

FIG. 1A details the structures of the phosphoramidate modified internucleoside linkages compared in this invention. The neutral 2-methoxyethylamine derivative on the left and the N,N-diethyl-ethylenediamine derivative (shown in an uncharged state) on the right. FIG. 1B lists the oligonucleotides used to form triplex structures of this invention. ODNs U-1, N-1, N-2, P-1, P-2, P-3 and P-4 bind in the major groove of Duplex I, as shown. All of the TFOs have the same sequence but are modified as follows: —=phosphodiester linkages, *=2-methoxyethylamine phosphoramidate linkages and +=N,N-diethyl-ethylenediamine phosphoramidate linkages. The percent of modified bonds are listed to the right of each ODN. Duplex II represents an unrelated, nontarget polypurine:polypyrimidine duplex.

DETAILED DESCRIPTION OF THE INVENTION

The present invention relates to the selection, production and use of oligonucleotides with cationic phosphoramidate modified internucleoside linkages to form stable triplex DNA structures to inhibit gene expression. The oligonucleotides of this invention, that is oligonucleotides with cationic phosphoramidate modified internucleoside linkages, can be prepared to bind to a variety of duplex DNA sequences and therefore have a wide range of applications for inhibiting transcription.

For example, transcription level-altering oligonucleotide-directed strategies can be and have been directed to a variety of cancers due to inappropriate gene activation, including leukemias (such as the use of oligonucleotides to purge bone marrow cells of leukemic progenitors prior to bone marrow transplantation) or cancers associated with oncogene activation. These types of strategies can benefit from the oligonucleotides of this invention. The oligonucleotides of this invention can also be used to control or limit vital infection (including but not limited to HIV, members of the Herpesvirus family including HSV, CMV or VZV as well as other viruses where transcription is directed from duplex DNA) or other intracellular pathogens through the suppression, alteration or reduction of gene expression (for a general discussion see Askari, et al. *New Engl. J. Med.* 334(5):316–318, 1996). These oligonucleotides can also be used in triplex-forming strategies for a variety of metabolic diseases including inborn errors of metabolism, hypotension and cardiovascular disease (such as oligonucleotides engineered to inhibit cellular proliferation to prevent restenosis due to cellular hyperplasia).

As a first step in practicing this invention, target DNA is selected. Preferably the target DNA for triplex formation is selected from the regulatory region of a gene whose expression is targeted for depletion. The particular target regions can come from any of a variety of regulatory regions within the DNA including but not limited to the promoter, the transcriptional start site, or 5' of the transcriptional start site, enhancers or promoters. Promoter regions are preferred and methods for identifying the promoter region of a particular gene are known in the art.

Currently, regions appropriate for triplex formation require the identification of consecutive purines on one strand in a region that overlaps or encompasses the binding site for a protein:DNA complex. The mechanism of action in this case, depends upon competition for the same hydrogen binding sites found in the major groove. This region is preferably upstream from the methionine start site. In general, the longer the stretch of purines, the more stable the complex and the better the binding of the oligonucleotide. Our in vitro evidence suggests that a region with at least fifteen purines with two pyrimidine interruptions is adequate for triplex formation.

Where the target site is within a promoter, formation of a triplex in that promoter region adjacent to a protein binding region can also disrupt binding, therefore sites around the DNA:protein interaction domains are also suitable target sites (for example, see Maher, et al. (1991) "Inhibition of DNA/protein Interactions" in *Prospects for Nucleic Acid Therapy of Cancer and AIDS* pp. 227–242, Wiley Liss, Inc.). The effect of binding of the oligonucleotide to a target region within a promoter could interfere with the proper association of the promoter and transcriptional activators. When a specific target sequence is available for binding to protein it is likely that it will also allow binding to an oligonucleotide.

A second way that triple helix formation could inhibit gene expression is to act as a physical block to the transit of the polymerase complex. The target area in this case is positioned after the transcriptional start site. There are in vitro examples of triplexes serving as physical blocks to transcription.

A third way that triplexes might disrupt transcription is by introducing structural changes that affect the ability of the polymerase complex to initiate transcription, thus, targeting areas upstream but close to the transcription initiation site may allow testing of this type of transcription initiation.

To summarize, the more that is known about a promoter, the better the chance of altering gene expression. In many cases, the site of binding of an activator protein is known and the sequence conforms to the definition of purine rich (at least 13 out of 17 purines in a stretch of 17 nucleotides). The term GA rich refers to at least 10 of the 17 purines being either G or A. This sequence may be part of an enhancer or adjacent to a known protein binding domain. When little is known about the regulation of the gene, any purine stretch is a potential target that can be tested in vitro using the exemplary methods disclosed in the examples that can be adapted to any of a variety of target duplex DNA sequences and potential triplex forming oligonucleotides.

Methods for sequencing a particular gene or the upstream regulatory regions of a gene are known in the art; therefore, these methods will not be detailed here. Once the 5' start site and/or regulatory regions of the gene are identified, this region is sequenced and reviewed. A target region of preferably between 17–100 nucleotides of double stranded DNA is selected and more preferably a region of between 17–50 nucleotides of double stranded DNA is selected. One or more oligonucleotides are designed to bind to one or more regions of the target double stranded DNA.

The sequence of the oligonucleotide will depend on the sequence of the targeted double stranded DNA. While sequences of purines are preferred for triplex formation using unmodified nucleoside bases, oligonucleotides having, for example, $N^3$-protonated deoxycytidine modifications can be used to make pyrimidine based triplex forming oligonucleotides that escape pH dependent binding to DNA duplexes (Karwczk, et al. supra) It is believed that base modifications to accommodate triplex formation by pyrimidine triplex forming oligonucleotides can be combined with the cationic phosphoramidates of this invention and that such modifications can be made and tested in view of this disclosure without undue experimentation. All triplex forming oligonucleotides are expected to benefit from the stability imparted by the cationic phosphoramidate internucleoside linkages of this invention.

In the purine triplex motif adenosine bases in the target duplex can interact with either A or T residues. The TFOs in this invention are designed to be GA rich instead of GT rich. The T residues in a GT rich ODN may encourage intracellular guanine quartet formation by providing points of stable hairpins. This idea is supported by examining human telomeres, structures known to form G quartets (Williamson, et al. *Cell*, 59:871–880, 1989). Human telomeres contain numerous repeats of the sequence TTAGGG, exhibiting an enhancement of T residues and a paucity of A residues.

Among the trials that serve to predict efficacy for triplex forming oligonucleotides are a series of in vitro trials using the targeted duplex and purine motif triplex forming oligonucleotides. As one way of identifying preferred oligonucleotides and as disclosed in Example 5, apparent binding constants for each triplex forming oligonucleotide may be determined and the triplex forming oligonucleotide with the best binding is used for in vitro and in vivo analysis of transcriptional inhibition.

The length of the oligonucleotide can vary. Preferably the oligonucleotides are from about 15 bases in length to about 50 bases in length with a most preferably length of about 15 to about 30 and still more preferably of about 17 to about 24 bases.

Once the sequence of the oligonucleotide has been designed or selected, the oligonucleotide can be synthesized. There are a variety of methods known in the art for synthesizing oligonucleotides. Most notably, oligonucleotides can be synthesized manually or using automated DNA synthesizers employing H-phosphonate monomers and chemistry. These methods are known in the art and for that reason will not be detailed here. The oligonucleotides of this invention incorporate modified internucleoside linkages. Cationic phosphoramidates are used to replace at least one phosphodiester linkage. In a preferred embodiment, the cationic phosphoramidate is N,N-diethyl-ethylenediamine; however, other classes of ethylenediamines are also contemplated in this invention, including but not limited to ethylenediamine and N-ethyl-ethylenediamine. Essentially any compound that can be added by oxidative amidation could be tested using the guidelines provided in this disclosure. Other cationic phosphoramidates suitable as substitutes for phosphodiester internucleoside linkages include, but are not limited to diaminobutane and polylysine.

This invention incorporates cationic phosphoramidate linkages during oligonucleotide synthesis. Oligonucleotides can be prepared with a single cationic phosphoramidate internucleoside linkage, or up to 100% of the internucleoside linkages can be prepared using cationic phosphoramidates. In a preferred embodiment, the range of substituted linkages is between 30–100% and in another particularly preferred embodiment, the range is between 60–100% cationic phosphoramidate substituted linkages.

Example 1 details a preferred method for preparing oligonucleotides with cationic phosphoramidate linkages, where the cationic phosphoramidate is N,N-diethyl-ethylenediamine. Since the class of cationic phosphormidates of this invention are used to create internucleoside linkages by oxidative amidation, the chemistry for synthesizing oligonucleotides using other cationic phosphoramidates will not differ significantly and those skilled in the art of oligonucleotide modifications will be readily able to prepare a variety of other oligonucleotides with other cationic phosphoramidate linkages without undue experimentation.

A number of oligonucleotides were prepared that varied in the amount of cationic phosphoramidate internucleoside linkages, as illustrated in FIG. 1. Oligonucleotides with these modified cationic linkages were compared to oligonucleotides containing neutral linkages. FIG. 1A illustrates the structure of a preferred cationic phosphoramidate modification used in this study. The methoxyethylamine derivative was used to generate oligonucleotides with neutral internucleoside linkages. Solubility of the derivative was enhanced through hydrogen bonding between water and the ether oxygen. The N,N-diethyl-ethylenediamine derivative is shown uncharged but is protonated (and hence, positively charged) at physiologic pH.

In one example of this invention, the sequence of the target region was derived from the enhancer of the GS17 gene of *Xenopus laevis* (Ovsenek, et al. *Development*, 115:649–655, 1992). Duplex I (SEQ ID NO:1) is 30 bp in length and contains a 17 bp purine rich region. The presence of pyrimidines on the purine rich strand makes this region an imperfect triplex forming consensus sequence but likely represents a more commonly available target than the 25–35 bp target region within the myc gene containing an uninterrupted polypurine:polypyrimidine sequence that is often used for in vitro studies.

The ODNs used in one example in this study are identical in nucleic acid sequence and correspond to SEQ ID NO:2. Each oligonucleotide illustrated in FIG. 1B contains either no modifications (oligo U-1), neutral internucleoside linkages (N-1 and N-2) or cationic phosphoramidate internucleoside linkages (P-1 through P-4). In designing the TFOs, thymidine was chosen to interact with the 2 C:G inversions based on a report demonstrating significant T.C:G binding (Durland, et al. *Nucleic Acids Research*, 22:3233–3240, 1994). N-1 and N-2 represent identical oligonucleotides containing 7 and 11 neutral methoxyethyl phosphoramidate linkages, respectively. These neutral bonds are represented by * in FIG. 1. ODNs P-1 through P-4 contain increasing numbers of positively-charged N,N-diethyl-ethylenediamine phosphoramidate linkages, from 9 to 16. The positive linkages are represented as + in FIG. 1. The extent of modification of each ODN is indicated to the right of the sequence.

The positive internucleoside linkage was made by amidation of the corresponding hydrogen phosphonate diester with N,N-diethyl-ethylenediamine as described in Example 1. N,N-diethyl-ethylenediamine is preferred to N-ethyl-ethylenediamine or ethylenediamine for triplex formation under physiologic conditions because it possesses both primary and tertiary amine moieties. The primary and tertiary amine moieties allow for a more specific reaction and minimize oxidative amidation at each end of the diamine. Oxidative amidation has the potential for crosslinking oligonucleotides. Moreover, the pKa of a tertiary amine is higher than that of the corresponding primary or secondary amine. The resulting increased degree of protonation of the ODN produces a greater net positive charge at physiologic pH.

Once target duplex has been identified and oligonucleotides are synthesized, synthetic target duplex can be prepared to test the ability of the synthesized oligonucleotides to bind to the target duplex under physiologic conditions. The oligonucleotides provided in FIG. 1 were tested in vitro and the ability of the oligonucleotides containing neutral internucleoside linkages to form triplex structures was compared to the triplex forming ability of oligonucleotides with cationic phosphoramidate substituted linkages. Example 3 details methods for testing triplex formation in vitro using both negatively charged, neutral and positively charged oligonucleotides.

Experiments were performed to test for the ability of a particular modified oligonucleotide to bind to duplex DNA. Example 4 details the results of binding studies to assess triplex formation between an unmodified negatively charged oligonucleotide and oligonucleotides N-1 and N-2, where negative charges were replaced with uncharged phosphoramidates. These experiments were performed in 10 mM $Mg^{2+}$ without potassium with ODN concentrations ranging from 20 nM to 2 µM. Triplex formation was found to be more efficient as negative phosphodiester linkages were converted to neutral phosphoramidate derivatives. Without limiting the scope of this invention, the most likely explanation for this observation is that the oligonucleotides containing the uncharged phosphoramidates carry a significant net negative charge and are repulsed, although less than unmodified oligonucleotide U-1, by the negative charge density of duplex I.

The requirement for relatively high concentrations of $Mg^{2+}$ in order to form triplex DNA using the neutrally modified ODNs supports the hypothesis that charge remains a major factor affecting triple strand association. increases in triplex formation can result from either increased affinity for the DNA duplex or decreased tendency toward formation of guanine quartets. The latter could increase the effective concentration of the TFO. Any ODN modification, whether directed at the bases, the sugar moiety or the phosphate backbone, has the potential to affect either or both of these equilibria.

In contrast to the oligonucleotides containing neutral modifications, nearly complete conversion of duplex DNA to triplex DNA was observed with the cationic phosphoramidates tested (see Example 5). The formation of triplex DNA in the presence of $K^+$ is important in determining whether the cationic phosphoramidates of this invention are useful in vivo. Example 6 details the effect of potassium chloride on triplex formation using the cationic phosphoramidates of this invention. The cationic phosphoramidate substituted oligonucleotides were significantly better at forming triplex structures than their unmodified or neutral counterpart. Moreover, increasing the amount of cationic internucleoside linkages increased the amount of triplex formation.

Triplex formation in the presence of LiCl, NaCl and KCl was evaluated to determine whether the observed triplex inhibition was potassium-specific or resulted from increases in the ionic strength of the solution. Example 7 discloses methods for assessing the effect of various monovalent cations at concentrations of 40, 80 and 120 mM on triplex formation. Triplex formation was least affected by increasing concentrations of LiCl, NaCl caused an intermediate level of inhibition and KCl had the greatest effect on triplex formation.

The effect of extensive cationic phosphoramidate modification on triplex formation was examined with oligonucleotides containing 88% modified linkages and 100% modified linkages (see Example 8). The ability of these oligonucleotides to associate with target duplex DNA was compared to unmodified oligonucleotides with the same base sequence at 130 mM $K^+$ and 1 mM $Mg^{2+}$, concentrations that approach physiologic salt concentrations. Oligonucleotides with extensive cationic phosphoramidate linkage modification demonstrated an improved capacity to form triplex structures.

The oligonucleotides were also tested for their capacity to form triplex DNA structures under stringent salt conditions (see Example 9). Results demonstrated that triplex formation with oligonucleotides containing increasing levels of cationic phosphoramidate linkages were less sensitive to $K^+$ concentration. Unexpectedly, almost 90% of Duplex I was in the triplex form at 250 mM KCl. Lane 13 shows duplex I in the absence of any TFOs. Increasingly positively-charged internucleoside linkages from 11 of 16 (69%) in P-2 to 14 of 16 (88%) in P-3 is associated with a associated with a significant decrease in potassium-mediated inhibition of triplex formation. In addition, and also unexpectedly, although magnesium is known to stabilize traditional triplex DNA, the results of Example 10 indicated that oligonucleotides with extensive cationic phosphoramidate modifications were essentially unaffected by $Mg^{2+}$ at physiologic $K^+$ concentrations.

This invention demonstrates that positively-charged ODNs with cationic phosphoramidate modified internucleoside linkages are significantly more effective in forming triplex DNA than the corresponding unmodified or neutrally-modified compounds. When an ODN is designed to interfere with intracellular nucleic acid metabolism, specificity becomes a crucial issue. Nonspecific electrostatic interactions between positively-charged ODNs and nontarget duplex DNA are a potential concern with these compounds. Example 11 discloses methods for testing the specificity of the oligonucleotide for its target using unmodified and cationic phosphoramidate modified oligonucleotides.

A second double stranded DNA strand nonspecific for the oligonucleotide (SEQ ID NO:3) was used to demonstrate the specificity of the oligonucleotides of this invention for their target duplex DNA. Duplex II, illustrated in FIG. 1, is a random, polypurine:polypyrimidine 30 bp sequence with 5 inversions. This duplex is used to measure nonspecific binding of a positively-charged ODN to a DNA duplex and as disclosed in the examples, is used to assess triplex forming oligonucleotide specificity. The sequence is found in the GS17 promoter, just downstream of the oligonucleotide target site. This sequence is random, with respect to the selected oligonucleotides designed to bind to the GS17 promoter and can therefore be used to assess specificity for any oligonucleotide that is targeted for triplex formation at a particular duplex DNA sequence; however, those skilled in the art will also appreciate that other duplex sequences can be used to assess the binding specificity of other oligonucleotides and that it is possible to produce nonspecific duplex DNA fragments from regions near or adjacent to a given targeted duplex DNA sequence to assess nonspecific binding as well.

To further investigate these nonspecific interactions under salt concentrations more closely resembling in vivo conditions, the experiment was repeated in 130 mM KCl. Oligonucleotides with extensive cationic phosphoramidate modifications had reduced nonspecific binding to duplex II under physiologic concentrations of $K^+$.

The inability of purine rich ODNs to form triplex DNA in the presence of physiologic concentrations of $K^+$ is a major hurdle in the development of oligonucleotide compounds as regulators of gene expression. This invention describes a class of positively charged ODNs that can efficiently form triplexes in the presence of physiologic and even supraphysiologic levels of potassium.

Replacing negative phosphodiester bonds with positively-charged phosphoramidate linkages resulted in compounds that more efficiently formed triplexes with double stranded target DNA. A progressive increase in triplex forming ability was observed with increasing positive charge. As discussed above, this was demonstrated by: 1) a decrease in $K_d$ with increasing ODN modification, 2) a decreased sensitivity to the inhibitory effects of monovalent cations on triplex formation, and 3) a diminished requirement of $Mg^{2+}$ in order to form triplex DNA. Without intending to limit the scope of this invention, because of the $Mg^{2+}$ independence of triplex association observed using oligonucleotides with at least 80% cationic phosphoramidate modified linkages, it is likely that electrostatic attraction between the ODN and the target duplex is a predominant force stabilizing the triplex. In addition to electrostatic attraction, it is possible that positively charged ODNs will have a reduced capacity to form guanine quartets and that both mechanisms could act to promote triplex formation.

A second benefit of the oligonucleotides of this invention as compared to other positively-charged oligonucleotides is the reduced levels of nonspecific association between cationic phosphoramidate modified oligonucleotides with non-target duplex DNA. Under physiologic levels of potassium chloride, the nonspecific binding of oligonucleotides with greater than 80% cationic phosphoramidate modification was nearly undetectable. Thus, under conditions that more closely approach physiologic, the extent of nonspecific triplex formation becomes minimal.

A third benefit of the oligonucleotides of this invention is that the cationic phosphoramidate modified internucleoside linkages, like other internucleoside modifications are resistant to RNase activity. This resistance enhances stability of the oligonucleotide in the cell.

The cationic phosphoramidate modified oligonucleotides of this invention can additionally incorporate other oligonucleotide modifications known in the art. For example, the oligonucleotide may include base modifications including, but not limited to 6-thioguanine base substitutions for purine:purine motif triplex forming oligonucleotides (Olivas, W. M. and Maher, L. J. III *Nucleic Acids Res.*, 23:1936–1941, 1995 and Rao, T. S., et al. *Biochemistry*, 34:765–772, 1995). Alternatively $N^3$ protonated deoxycytidine analogs can be incorporated into oligonucleotides for pyrimidine:purine motif triplex forming oligonucleotides (see Froehler, et al. *Nucleic Acids Res.*, 14:5399–5407, 1986). Other base modifications that could also be incorporated into the oligonucleotides of this invention include, but are not limited to methyl cytidine and alkynyl base modifications.

In addition, the oligonucleotides can be labelled with fluorescent tags including but not limited to fluorescein, Rhodamine Green, Rhodamine Red, Texas Red, Biotin, DNP, and the like (see, for example FluoReporter Oligonucleotide Amine Labeling Kits provided by Molecular Probes, Eugene ORE). Suitable chromophores are those with amine groups that can be added by oxidative amidation. In addition, chromophores with isothiocyanate groups can also be used. These can be added to the oligonucleotide during synthesis using oxidative amidation of H-phosphonate diester with diamine or can be reacted with available amines. Similarly, the oligonucleotides of this invention can be coupled to haptens or any of a variety of fluoroprobes that do not interfere with the binding characteristics of the modified oligonucleotides for their target DNA. These oligonucleotides can be used to monitor binding of the labelled oligonucleotide to duplex DNA.

Once the oligonucleotides have been tested for their binding affinity to target duplex DNA, the cationic phosphoramidate modified probes of this invention can be tested in vitro to determine in vivo efficacy. There are a variety of methods known in the art for introducing oligonucleotides into cells in vitro. These methods include, but are not limited to, microinjection, liposome technology including antibody directed liposomes or antibody directed oligonucleotides as well as non targeted liposomes.

As a preferred testing regime, the oligonucleotides are microinjected into cells obtained from animal or man. The cell type chosen is determined by the presence or absence of the selected target DNA in the cell type. As one example, the target DNA is a sequence of duplex DNA from the enhancer region of the GS17 gene of *Xenopus laevis*, corresponding to Duplex I of FIG. 1 and the oligonucleotides tested have the nucleic acid sequence and base modifications of oligonucleotides P-3 and P-4 of FIG. 1. Although embryos and oocytes from *Xenopus laevis* are used in these studies and the target duplex DNA is the GS17 gene, oligonucleotide delivery to a variety of cells is known in the art and those skilled in the art will recognize the applications of these examples to a wide variety of target duplex DNA sequences resident in a variety of eukaryotic cells.

There are two factors that are assessed in determining the ability of a particular oligonucleotide to mediate an inhibitory effect on transcription; toxicity of the oligonucleotide to the cell and effect of the oligonucleotide on targeted transcriptional inhibition. Example 12 details methods for assessing the cellular toxicity of the oligonucleotide and Example 13 discusses methods for assessing the effect of the cationic phosphoramidate modified oligonucleotide on transcriptional inhibition. Reduction in transcription rates is analyzed by measuring either mRNA levels produced by the targeted genes or by assaying for levels of the protein product encoded by the mRNA. Methods for measuring both mRNA and protein production from a cell are well known in the art.

Once an inhibitory effect has been observed in vitro, it is contemplated that the oligonucleotides of this invention can be used to impart a transcriptional impact on eukaryotic cells ex vivo and in vivo. Thus in one embodiment of a method for inhibiting expression of a gene in an animal, a cell sample is removed from an animal, and processed to produce a cell sample that can be treated with the oligonucleotides of this invention using, for example the methods disclosed in PCT patent application WO 9411524 to Anderson, et al. In a second embodiment, the oligonucleotides of this invention are encapsulated in lipids, using the methods and techniques disclosed in PCT published patent applications Wo 9517373 to Ciccarone, et al., WO 9014074 to Abai, et al. U.S. Pat. No. 5,194,654. The lipid/oligonucleotide formulation is delivered to the animal or human by parenteral or oral routes of administration including but not limited to intravenous, subcutaneous, intramuscular, mucosal introduction such as through the use of aerosols or drips, and alimentary introduction. Those skilled in the art will recognize that the choice of delivery will be determined by the source of cells containing duplex DNA targeted for gene expression inhibition.

Those skilled in the art will recognize that there are a variety of modifications which can be made to oligonucleotides to facilitate cellular uptake. Similarly, a number of studies have been performed that address methods for delivery of a variety of oligonucleotides to cells in a mammal. All references cited throughout this text are herein expressly incorporated by reference.

EXAMPLE 1

Oligonucleotide Synthesis

Modified ODNs were synthesized on an ABI model 391 PCR-mate DNA synthesizer using hydrogen phosphonate chemistry (Froehler, et al. *Nucleic Acids Res.* 14: 5399–5407, 1983). All reagents used for automated DNA synthesis were obtained from Glen Research (Sterling, Va.). To generate unmodified phosphodiester bonds, hydrogen phosphonate diesters were oxidized for 4 min with freshly prepared 5% iodine in THF:pyridine:water (15:2:2) and then 3 min with the same solution diluted 1:1 with 8% TEA in THF:water (43:3). Oxidative amidation of hydrogen phosphonate diesters was performed manually using a 10% solution of either 2-methoxyethylamine or N,N-diethylethylenediamine (Aldrich) in anhydrous $CCl_4$ as previously described (Dagle, et al. *Nucleic Acids Res.* 18:4751–4757, 1990). ODNs containing both phosphodiester and phosphoramidate linkages were synthesized in blocks. The desired number of 3' residues was first coupled and then either oxidized or oxidatively amidated. The next block of residues was then individually condensed and subsequently oxidized or oxidatively amidated. Purification of ODNs was performed as described previously (Dagle, *Nucl. Acids Res.* supra). Following Sephadex G-25 column chromatography (Pharmacia) to remove small molecular weight impurities, ODNs were dissolved in sterile water and quantitated by UV spectroscopy. It was assumed that the modified linkages did not significantly effect the extinction coefficients of the individual ODNs. ODN heterogeneity was assessed using denaturing reversed-polarity gel electrophoresis. The presence of a distinct band was indicative of a homogenous oligonucleotide population.

EXAMPLE 2

Oligonucleotide Labeling

Target duplexes are formed from a 1:1 mixture of complementary unmodified 30-mer ODNs which are heated to 80°

C. for 5 min and allowed to slowly cool to room temperature. These duplexes were 5' end-labeled with T4 polynucleotide kinase (Promega, Madison Wis.) and $\gamma$-$^{32}$P-ATP (6000 Ci/mmole, Amersham). 2 pmol of DNA duplex (4 pmole of 5' ends) was incubated at 37° C. for 45 min under the following conditions: 70 mM Tris pH 7.6, 10 mM MgCl$_2$, 5 mM DTT, 8 pmole ATP and 3 U T4 polynucleotide kinase in a total of 10 ul. The reaction was stopped by the addition of 90 μl of 7.5M ammonium acetate and subsequent phenol:chloroform extraction. The aqueous phase was added to 20 μg of carrier glycogen. To this was added 300 μl ethanol and the solution was kept at −70° C. for at least 30 min. Following centrifugation, the pellet was resuspended in water to a concentration of 10 nM.

EXAMPLE 3

Triplex Formation Assay

Triplex formation was initiated by the addition (in order) of 5 μl H$_2$O, 2 μl 5x buffer (100 mM Tris-HCl pH 7.5, 0 to 50 mM MgCl$_2$), 1 μl labeled DNA duplex (2–10 femtomoles), 1 μl yeast tRNA (1 mg/ml), and 1 μl triplex forming ODN. The buffer solutions and ODN concentrations were altered to examine triplex formation under various conditions. The mixtures were incubated at ambient temperature overnight. After the addition of 1 μl of gel loading buffer (0 to 10 mM MgCl$_2$ to match the assay conditions, 20 mM Tris-HCl pH 7.5, 50% glycerol and 0.05% each bromophenol blue and xylene cyanol), the samples were loaded onto a 15% polyacrylamide (acrylamide:bisacrylamide= 100:1) gel and analyzed by nondenaturing gel electrophoresis. The electrophoresis buffer was TMB (90 mM Tris base, 90 mM boric acid, and 10 mM MgCl$_2$). Electrophoresis was performed at 4° C. for 4–6 hr. The gel was dried under vacuum and exposed at −70° to Kodak X-OMAT AR film using an intensifying screen. The amount of radioactivity present in the duplex and triplex forms was determined by electronic autoradiography (InstantImager, Packard, Downers Grove, Ill.). The fraction of target duplex bound by a TFO, $\Theta$, was calculated using the equation:

$$\Theta = S_{triplex}/(S_{triplex} + S_{duplex})$$

where $S_{duplex}$ and $S_{triplex}$ represent the electronic autoradiographic signal for the duplex and triplex bands, respectively. The Kd for an ODN in triplex formation was determined from the concentration of the compound which causes ½ of the target duplex to shift to the triplex form.

EXAMPLE 4

Effect of Charge Neutralization on Triplex Formation

Negative charges were removed from the oligonucleotide of FIG. 1 and replaced with neutral charges using the methoxyethylamine derivative illustrated in FIG. 1. ODNs N-1 and N-2 were compared with their unmodified counterpart, U-1, for the ability to form triplexes with duplex I. These experiments were performed in 10 mM Mg$^{2+}$ and no K$^+$, with ODN concentrations of 0 nM, 20 nM, 200 nM and 2 μM for each of the three oligonucleotide samples. A gel shift assay was performed. Triplex formation was seen with increasing concentrations of U-1, N-1 and N-2. Triplex formation was more efficient as negative phosphodiester linkages were converted to neutral phosphoramidate derivatives. 2 μM of unmodified oligonucleotide shifted a small amount of duplex I. With decreasing negative charge, an increasing fraction of duplex I was shifted to the more slowly migrating triplex form.

EXAMPLE 5

Triplex Formation with ODNs Containing Positively-Charged Internucleoside Linkages ODNs P-1 and P-2 were also compared to the unmodified oligonucleotide, U-1, in a gel shift assay. The assay was performed in 1 mM MgCl$^2$ and no K$^+$ and demonstrated a significant increase in triplex formation in those oligonucleotides with positively-charged internucleoside linkages. Interestingly, U-1 is unable to shift more than 15% of duplex I to a more slowly migrating form at 2 μM, the highest ODN concentrations examined. No distinct triplex band was visible. In contrast, nearly complete conversion of duplex to a distinct triplex was observed with oligonucleotides P-3 and P-4 over the 2 nM to 2 μM concentration range tested (samples were tested at 2 nM, 20 nM, 200 nM and 2 μM). The Kd for U-1 could not be measured under these conditions, the Kd for P-1 was about $8\times10^{-7}$M, while that of P-2 was about $8\times10^{-8}$M.

EXAMPLE 6

Triplex Stability in the Presence of Potassium

At 1 mM MgCl$_2$ and 0 mM KCl, ODNs containing several positively-charged internucleoside linkages were superior to their unmodified counterpart in triplex formation. The formation of triplex DNA in the presence of K$^+$, however, is crucial if these oligonucleotides are useful in inhibiting gene expression in vivo. Positively-charged ODNs P-1 and P-2 are compared to U-1 at 2 concentrations each of both MgCl2 and KCl. The ODN concentration used was 200 nM. Oligonucleotide U-1 was examined at 1 mM and 10 mM MgCl$_2$, while oligonucleotides P-1 and P-2 were examined at the more stringent conditions of 0.1 MgCl$_2$ and 1 mM MgCl$_2$. A trace amount of shifted duplex was seen by gel shift assay with ODN U-1 at 10 mM MgCl$_2$, but not at 1 mM MgCl$_2$. In contrast, ODN's P-1 and P-2 formed triplex DNA at both 0.1 nM MgCl$_2$ and 1 mM MgCl$_2$. In both cases there was only a slight increase in triplex at 1 mM MgCl$_2$ compared to 0.1 mM MgCl$_2$. The response of P-1 compared to P-2 with respect to K$^+$ inhibition was striking, especially at 1 mM MgCl$_2$. Triplex DNA formation seen with P-2 at 1 mM MgCl$_2$ and 100 mM KCl was approximately 80% of that seen without KCl. In contrast, triplex DNA formed with P-2 at 0.1 mM MgCl$_2$ and 100 mM KCl was reduced to less than 60% of that seen without KCl. This monovalent cation-inhibition of triplex formation is similar to that reported by other laboratories with unmodified ODNs (Milligan, et al. *Nucleic Acids Res.*, 21:327–333, 1993; Cheng,A.-J., et al. *Nucleic Acids Res.*, 21: 5630–5635, 1993; and Olivas, et al. *Biochem.* supra,).

EXAMPLE 7

Triplex Formation in the Presence of Monovalent Cations

Triplex formation in the presence of LiCl, NaCl and KCl was evaluated to determine whether the observed triplex inhibition was potassium-specific or resulted from increases in the ionic strength of the solution. ODN P-2 was studied at a concentration of 2 μM with a Mg$^{2+}$ concentration of 0.1 mM using 40, 80 and 120 mM concentrations of LiCl, NaCl or KCl. Triplex formation was least affected by increasing concentrations of LiCl. NaCl caused an intermediate level of inhibition and KCl had the greatest effect on triplex formation. This pattern of monovalent cation inhibition was identical to that seen with unmodified ODNs suggesting a similar mode of association of the oligonucleotide to the duplex.

EXAMPLE 8

Triplex Formation using Oligonucleotides with Extensive Cationic Phosphoramidate Modifications The effect of extensive ODN modification on triplex formation was examined with oligonucleotides containing 88% modified linkages or 100% cationic phosphoramidate modified linkages (P-3 and P-4, respectively). The ability of ODNs P-3 and P-4 to associate with duplex I was compared to that of compounds U-1 and P-2. The assay was performed using 130 mM $K^+$ and 1 mM $Mg^{2+}$, concentrations that approximate physiologic salt concentrations. The ODN concentrations used were 20 nM, 200 nM and 2 µM. Samples were processed with the various oligonucleotides at the various concentrations and a sample containing no oligonucleotide was used as a background control. Shading in the control lane, located in the region where the triplex band migrated was subtracted from the triplex bands during data analysis. Triplex formation with U-1 was essentially undetectable under the concentrations tested. Both P-3 and P-4 showed a greater affinity, and therefore, improved stability, for duplex I than did P-2. The dissociation constants for triplex formation were $8 \times 10^{-7}$M for P-2, $1 \times 10^{-7}$M for P-4 and $7 \times 10^{-8}$M for P-3. The migration of the triplex formed with P-3 was slightly slower than that with P-2, a result of the increased cationic nature of P-3.

EXAMPLE 9

Triplex Formation under Stringent Salt Conditions

The effect of increasing KCl concentrations on triplex formation was also assessed. Oligonucleotides P-2 and P-3 were incubated with duplex I under increasing concentrations of KCl (0, 50, 100, 150, 200 and 250 mM). The concentration of $MgCl_2$ was held at 1 mM and the ODN concentration was 2 µM. Increasing concentrations of KCl gradually reduced the amount of triplex DNA observed for oligonucleotide P-2; however, significant triplex formation was observed at physiologic levels of potassium. The inhibitory effect of KCl appeared to plateau at 200 mM, as no further triplex inhibition was observed at 250 mM. Triplex formation with ODN P-3 was significantly less sensitive to $K^+$ concentration, in fact, at 250 mM KCl, almost 90% of Duplex I remained in the triplex form. Increasingly positively-charged internucleoside linkages from 11 of 16 (69%) in P-2 to 14 of 16 (88%) in P-3 is associated with a significant decrease in potassium-mediated inhibition of triplex formation.

EXAMPLE 10

Magnesium Requirements for Triplex Formation $Mg^{2+}$ is known to stabilize traditional triplex DNA. The effect of decreasing $Mg^{2+}$ and increasing $K^+$ on triplex formation was assessed using ODNs P-2 and P-3 by gel shift assay. In the absence of $K^+$, triplex formation with both P-2 and P-3 was essentially unaffected by $Mg^{2+}$ concentrations ranging from 0 to 1 mM. Triplex formation was greater than 80%, even in the absence of $Mg^{2+}$. Although increased $Mg^{2+}$ concentration had no effect on the amount of triplex formed with P-3, in the absence of $K^+$ a small fraction of the triplex DNA changed to a more rapidly migrating form with increased $Mg^{2+}$. The appearance of this band with intermediate electrophoretic mobility suggests the possibility of different conformations of triplex DNA. In 130 mM KCl, triplex formation with ODN P-2 became sensitive to $Mg^{2+}$ concentration. There was a significant reduction in triplex DNA formed with oligonucleotide P-2 as $Mg^{2+}$ decreased from 1 mM to 0 mM. Triplex formation with P-3, remained essentially independent of $Mg^{2+}$ concentration in the presence of physiologic concentrations of KCl.

EXAMPLE 11

Oligonucleotide Specificity for Target DNA

Oligonucleotide P-4 was used to examine the specificity of the oligonucleotide for its target versus a random oligonucleotide such as duplex II. The nonspecific interaction of oligonucleotides U-1 and P-4 with the nontarget duplex II in the presence of either 1 mM or 10 mM $MgCl_2$ and in the absence of KCl were assessed by gel shift analysis. Binding of U-1 to duplex II was not detected and nonspecific interactions between P-4 and duplex II were not detected at ODN concentrations of 20 nM to 200 nM of oligonucleotide. The complex formed at about equal levels at both 10 mM $Mg^{2+}$ and 1 mM $Mg^{2+}$, indicating a lack of $Mg^{2+}$ dependence in this range of ion concentration. To further investigate these nonspecific interactions under salt concentrations more closely resembling in vivo conditions, the experiment was repeated in 130 mM KCl. Under conditions approximating physiologic, oligonucleotide U-1 again showed no evidence of binding to duplex II at either 1 mM or 10 mM $Mg^{2+}$. At an ODN concentration of 2 µM, the extent of nonspecific binding of P-4 to duplex II was greatly attenuated by increasing the $K^+$ concentration of the triplex buffer. In both cases the degree of nonspecific binding was too low for accurate quantitation. The decrease in nonspecific binding seen in 130 mM KCl was likely related to a general increase in ionic strength, however, it is also possible that there was a specific effect of $K^+$.

EXAMPLE 12

Toxicity Testing of Oligonucleotide for Target Cell

As an example of a method to determine whether or not the cationic phosphoramidate modified oligonucleotides are toxic to target cells containing the target duplex DNA, Xenopus embryos were microinjected with varying concentrations of oligonucleotide. *Xenopus laevis* were purchased from Xenopus I (Ann Arbor Mich.) Eggs were obtained from mature frogs fertilized in vitro and maintained in 0.1X MBSH (Colman, et al. (1984) In Hames, D. and Higgins, S. (ed.), *Transcription and translation-A Practical Approach*. IRL Press, Oxford, pp 271–302). Oligonucleotides were injected by microinjection into the cytoplasm of the embryos as described by Colman (supra). To study the degradation of the oligonucleotides, at various times following injection of labeled oligonucleotides (see Example 2), the injected embryos were frozen in dry ice and thawed in 200 µl chloroform and 400 µl 0.2% SDS, the phenol layer was extracted with water twice more. Aqueous fractions were pooled, extracted once with chloroform and dried in a SpeedVac Concentrator. The residue was resuspended in water and the amount of radioactivity was determined by scintillation counter or analyzed by electrophoresis using a 20% polyacrylamide-7M urea gel which was subsequently exposed at −70° C. to Kodak X-OMAT AR film with an intensifying screen.

To determine the cellular toxicity of the oligonucleotides, various concentrations of oligonucleotide were microinjected into matched cell samples. Defects in activation of gene expression, reflecting toxicity related to general inhibition of transcription is assessed by looking at the activation of specific genes that are expressed at the 4000 cell stage including GS17 or EF-Iα gene expression. In addition, defects in gastrulation, neurulation or other early developmental events serves as a sensitive measure of non-specific toxicity; therefore, this model is useful to test toxicity for oligonucleotides in general. (see Vize, et al. *Methods in Cell Biol.* 36:367–387, 1991). Embryos obtained as outlined in Weeks, et al. (1991, supra) have been injected with up to 10 ng of modified oligonucleotides as described herein without non-specific toxic affects. Further, experiments to determine the toxic dose of these modified oligonucleotides in vivo are under way. Uninjected and control injected (injection buffer alone) embryos are compared to oligonucleotides injected using groups of 50 embryos in experiments performed in triplicate. Defects are noted by comparison to *Xenopus laevis* normal tables (Nieuwkoop, et al. (1967) *Normal table of Xenopus laevis* (Daudin). North Holland Publishing Co., Amsterdam.

EXAMPLE 13

Effect of Oligonucleotides on Gene Expression

The most direct way of examining the effect of a TFO on gene expression is to measure RNA levels derived from the gene that is targeted. This measurement might be made by sampling tissue and extracting RNA followed by northern blot analysis, RNase protection assays or Reverse transcriptase PCR. All techniques well known in the art and discussed in detail in *Molecular Cloning: A Laboratory Manual* (Sambrook, et al. 1989, Cold Spring Harbor Laboratory, Cold Spring, N.Y.).

Alternatively, levels of RNA can be examined by in situ analysis of tissues of interest. These techniques are also known in the art. A less direct, but often useful way to look at transcription is to assay for the protein products of the gene. This would include Western analyses, polyacrylamide gel electrophoresis, and a variety of antibody based stratagies including radioimmunoassays and enzyme linked immunoadsorbent assays. All well known in the art. Sensitive measures of protein levels both from extracted tissues (including blood) or immunohistochemistry are known in the art. The effectiveness of introduction of TFO's into the bloodstream (as described for clinical trials on antisense oligo introduction for AID's therapy) or at the site of tumor growth can be assayed by regression of tumor size, or by sampling the tumor for decreases in growth rate, induced apoptotic events, or changes in myc RNA levels.

EXAMPLE 14

Using TFO's to Alter the Expression of the Myc Oncogene

One of the most common oncogenes expressed in transformed cells is the c-myc oncogene. In vitro inhibition of the c-myc oncogene has been reported (Kim, H-G and Miller, D. (1995) "Inhibition of In vitro transcription by a triplex forming oligonucleotide targeted to human c-myc P2 promoter", *Biochemistry* 34, 8165–8171). The oligonucleotides AGGGAGGGAGGTAAGAAAAAGGG (SEQ ID NO:4) and GGGAAAAAGAATGGAGGGAGGGA (SEQ ID NO:5) are prepared having 87% of the linkages substituted with N,N-diethyl-ethylenediamine as disclosed in Example 1. Triplex formation is demonstrated by electrophoretic mobility shift analysis of triplex formation and DNase I foot-printing as disclosed by Kim, et al. (supra). In vitro transcription alteration is performed using a HeLa nuclear extract in vitro transcription system (Promega) as disclosed by Kim, et al.

It will be appreciated that certain variations to this invention may suggest themselves to those skilled in the art. The foregoing detailed description is to be clearly understood as given by way of illustration, the spirit and scope of this invention being limited solely by the appended claims.

---

---

What is claimed is:

1. A triplex-forming oligonucleotide comprising about 30–100% ethylenediamine phosphoramidate internucleoside linkages.

2. The oligonucleotide of claim 1, wherein the oligonucleotide is about 15–30 nucleotides in length.

3. The oligonucleotide of claim 1, wherein the oligonucleotide has ethyl-ethylenediamine phosphoramidate internucleoside linkages.

4. The oligonucleotide of claim 3, wherein the oligonucleotide has N-ethyl-ethylenediamine phosphoramidate internucleoside linkages.

5. The oligonucleotide of claim 3, wherein the oligonucleotide has N,N-diethyl-ethylenediamine phosphoramidate internucleoside linkages.

6. The oligonucleotide of claim 5, wherein about 60–100% of the oligonucleotide internucleoside linkages are N,N-diethyl-ethylenediamine.

7. The oligonucleotide of claim 1, wherein the oligonucleotide is purine rich.

8. The oligonucleotide of claim 7, wherein the oligonucleotide is GA rich.

9. A triplex-forming oligonucleotide that is about 15 to about 30 bases in length and has at least one N,N-diethyl-ethylenediamine phosphoramidate internucleoside linkage.

10. The oligonucleotide of claim 9, wherein the oligonucleotide is purine rich.

11. The oligonucleotide of claim 9, wherein about 30–100% of the oligonucleotide internucleoside linkages are N,N-diethyl-ethylenediamine phosphoramidate linkages.

12. The oligonucleotide of claim 11, wherein about 60–100% of the oligonucleotide internucleoside linkages are N,N-diethyl-ethylenediamine phosphoramidate linkages.

13. The oligonucleotide of claim 9, wherein the oligonucleotide binds to the double stranded DNA antiparallel to the purine rich strand.

14. A triplex-forming oligonucleotide comprising more than one N,N-diethyl-ethylenediamine substituted phosphoramidate internucleoside linkage, wherein the oligonucleotide binds to double stranded DNA in a solution comprising a $K^+$ concentration of about 100–250 mM.

15. The oligonucleotide of claim 14, wherein the oligonucleotide is purine rich.

16. The oligonucleotide of claim 15, wherein the oligonucleotide is guanosine and adenosine rich.

17. The oligonucleotide of claim 14, wherein at least one guanosine is substituted by 6-thioguanosine.

18. A triplex-forming oligonucleotide comprising 60–100% N,N-diethyl-ethylenediamine substituted phosphoramidate internucleoside linkages.

19. A eukaryotic cell in culture containing an oligonucleotide having ethylenediamine substituted phosphoramidate internucleoside linkages, wherein said oligonucleotide binds to double stranded DNA in a solution comprising a $K^+$ concentration of about 100–150 mM, and wherein the ethylenediamine substituted phosphoramidate linkages are selected from the group consisting of ethylenediamine, N-ethyl-ethylenediamine and N,N-diethyl-ethylenediamine substituted phosphoramidate internucleoside linkages.

20. A method for stabilizing an oligonucleotide onto a DNA duplex strand under a potassium ion concentration of up to about 250 mM comprising the steps of:

selecting a region of duplex DNA having either a pyrimidine or a purine motif;

preparing an oligonucleotide that binds to the duplex DNA wherein the oligonucleotide comprises at least 30–100% ethylenediamine substituted phosphoramidate internucleoside linkages; and contacting the oligonucleotide with the duplex DNA in a solution comprising a potassium ion concentration of up to about 250 mM.

21. The method of claim 20, wherein the ethylenediamine substituted phosphoramidate internucleoside linkages of the preparing step are N,N-diethyl-ethylenediamine linkages.

22. The method of claim 20, wherein the oligonucleotide of the preparing step is about 15 to about 30 nucleotides in length.

23. The method of claim 20, wherein the oligonucleotide of the preparing step is purine rich.

* * * * *

UNITED STATES PATENT AND TRADEMARK OFFICE
CERTIFICATE OF CORRECTION

PATENT NO.: 5,734,040
DATED: March 31, 1998
INVENTOR(S): Daniel L. Weeks et al.

It is certified that error appears in the above-identified patent and that said Letters Patent is hereby corrected as shown below:

Col 1, line 16, please insert --The present invention was made with government support from the National Institutes of Health Grant No. HL 42266. The government has certain rights to this invention.--

Signed and Sealed this

Fifteenth Day of May, 2001

Attest:

NICHOLAS P. GODICI

Attesting Officer

Acting Director of the United States Patent and Trademark Office